(12) United States Patent
Omura et al.

(10) Patent No.: US 7,794,991 B2
(45) Date of Patent: Sep. 14, 2010

(54) STEMPHONES AND PRODUCTION THEREOF

(75) Inventors: Satoshi Omura, Tokyo (JP); Hiroshi Tomoda, Tokyo (JP); Rokuro Masuma, Tokyo (JP)

(73) Assignee: The Kitasato Institute, Tokyo (JP)

( * ) Notice: Subject to any disclaimer, the term of this patent is extended or adjusted under 35 U.S.C. 154(b) by 403 days.

(21) Appl. No.: 11/795,683

(22) PCT Filed: Oct. 3, 2005

(86) PCT No.: PCT/JP2005/004722

§ 371 (c)(1),
(2), (4) Date: Jul. 20, 2007

(87) PCT Pub. No.: WO2006/095444

PCT Pub. Date: Sep. 14, 2006

(65) Prior Publication Data

US 2008/0160587 A1     Jul. 3, 2008

(51) Int. Cl.
*C12P 17/06* (2006.01)
*C07D 311/94* (2006.01)

(52) U.S. Cl. .................... 435/125; 435/170; 435/256.1; 549/384

(58) Field of Classification Search ................. 435/125; 549/384
See application file for complete search history.

(56) References Cited

FOREIGN PATENT DOCUMENTS

| JP | 7-25880 | 1/1995 |
| JP | 9-509677 | 9/1997 |

OTHER PUBLICATIONS

Koyama et al. J. Antobiotics (Nov. 2005) 58(11): 695-703.*
Hasegawa, "MRSA," p. 264-273 (with translation).
Ogawara et al., "Inhibitors of Diacylglycerol Kinase from *Drechslera sacchari*," J. of Antibiotics, vol. 47, No. 4, pp. 499-501 (1994).

* cited by examiner

*Primary Examiner*—Sandra Saucier
*Assistant Examiner*—Susan Hanley
(74) *Attorney, Agent, or Firm*—Young & Thompson

(57) ABSTRACT

The present invention relates to novel stemphones having enhancing effect of β-lactam antibiotic used as an antibacterial agent, and a process for production thereof. The process is comprised of culturing microorganism belonging to genus *Aspergillus* and having ability to produce stemphones, the microorganism of which is *Aspergillus* sp. FKI-2136 NITE BP-83, accumulating the stemphones in the cultured mass, and isolating the stemphones from the cultured mass. Since the obtained stemphones have an action enhancing activity of β-lactam antibiotic used as an antibacterial agent by combining with β-lactam antibiotic, the stemphones are expected to be useful as the therapeutic agent for MRSA infection and infectious diseases caused by multi-drug resistant microorganisms including β-lactam antibiotic resistance.

5 Claims, 8 Drawing Sheets

STEMPHONES AND PRODUCTION THEREOF

This application is a national stage entry of PCT/JP05/04722, filed Oct. 3, 2005.

TECHNICAL FIELD

The present invention relates to novel stemphones having enhancing effect of β-lactam antibiotic used as an antibacterial agent, and a process for production thereof.

BACKGROUND ART

Recently, methicillin resistant *Staphylococcus aureus* (hereinafter designates as MRSA) has become a social problem as a major causative microorganism of hospital-acquired infection. This pathogenic microorganism is resistant to various medicines such as β-lactam antibiotic, and antibiotics such as glycopeptide antibiotic vancomycin and aminoglycoside antibiotic arbekacin, which are reported at present to exhibit almost no resistance, are generally used for treatment of MRSA. In addition to this, combination therapy of β-lactam antibiotics or that of β-lactam antibiotic and other antibiotic having different active site is employed at present (Yoshimi Hasegawa et al. "Science of antibiotic administration", p. 264-273, 1998).

Resistant strains against vancomycin and arbekacin have already appeared. It has become a problem that these antibiotics have been known to have adverse reaction to exhibit hearing impairment caused by eight cranial nerve disorder. In order to cope with these problems, a substance having an action for recovering effect of β-lactam antibiotic has been reported to date. For example, tea extract or active fraction thereof showing synergistic effect by using in combination with antimicrobial agent including βlactam antibiotic are agree with that (JP-A-9-509677). Since novel stemphones have an action for enhancing antimicrobial activity of imipenem, which belongs to carbapenem in β-lactam antibiotic, and at the same time have the action for enhancing antimicrobial activity of cloxacillin in penam as well as cefazoline in cephem, it is expected to apply for the combination therapy with antimicrobial agents including β-lactam antibiotic. Novel stemphones are clearly distinguished from the polyphenol compounds, which are the active ingredients of the tea extract or the active fraction thereof, in their molecular formulae and chemical structures.

DISCLOSURE OF THE INVENTION

It is expected that medicament enhancing activity of β-lactam antibiotic may reduce frequency of emergence of resistant bacteria by decreasing dosage of β-lactam antibiotic and shorten dosing period. It is also expected at the same time that resistance against β-lactam antibiotic may be overcome by combining two medicaments having different mode of action.

Under such circumstance, it will be useful that providing the substance having enhancing activity of β-lactam antibiotic against MRSA is to provide novel remedy for infectious diseases of MRSA and infectious diseases caused by multi-drug resistant bacteria including β-lactam antibiotic resistance.

The present inventors have explored a substance having activity with enhancing action for imipenem belonging to β-lactam antibiotic carbapenem with targeting metabolic products produced by microorganisms, and as a result, have found that a substance having activity with enhancing action for imipenem was produced in a culture of fungi FKI-2136 strain isolated newly from soil. Subsequently, we have isolated and purified two types of substance having activity with enhancing action for imipenem, and since substances having such the chemical structure have not been known, the substances were designated as stemphone B substance and stemphone C substance or simply designated as stemphone B and stemphone C, respectively, and were totally designated as stemphones.

The present invention has completed based on such knowledge, and an aspect of the present invention is to provide stemphones consisting of stemphone B represented by the following formula (I):

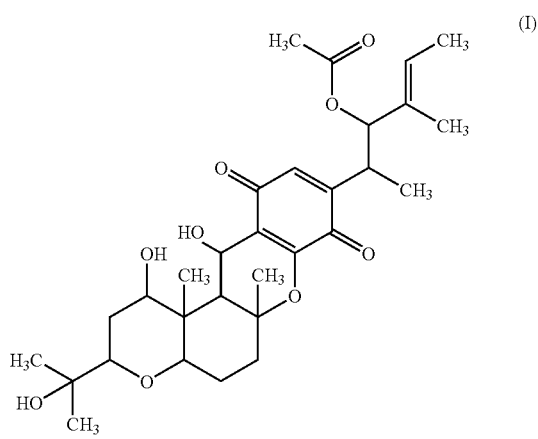

and/or stemphone C represented by the following formula (II):

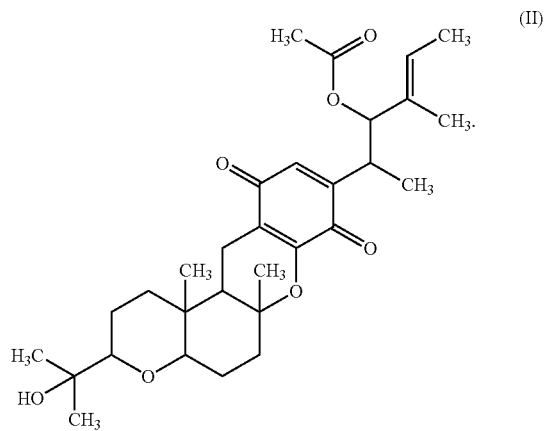

Another aspect of the present invention is to provide a process for production of stemphones comprising culturing a microorganism belonging to genus *Aspergillus* and having ability to produce stemphones represented by the aforementioned formula (I) and (II), accumulating stemphones in a cultured mass and isolating stemphones.

Further aspect of the present invention is to provide a process for production of stemphones wherein the microorganism belonging to genus *Aspergillus* and having ability to produce stemphones represented by the aforementioned formula (I) and (II) is *Aspergillus* sp. FKI-2136 NITE BP-83 or mutant thereof.

Further aspect of the present invention is to provide *Aspergillus* sp. FKI-2136 NITE BP-83.

The microorganism having ability to produce novel stemphones represented by the aforementioned formula (I) and (II) (hereinafter designates as "FKI-2136 substance producing microorganism") belongs genus *Aspergillus* and is acceptable if the microorganism has ability to produce stemphones of the present invention without limitation. Preferable example of the microorganism strain used for producing stemphones of the present invention is *Aspergillus* sp. FKI-2136 strain newly isolated from soil of Ishigaki-jima, Okinawa Pref. by the present inventors. Taxonomical properties of the strain are as follows.

1. Morphological Properties

The strain shows good growth on Czapeck yeast extract agar medium, malt extract agar medium and Czapeck yeast extract added with 20% sucrose agar medium, and good bearing conidiospore is observed.

When colonies grown on Czapeck yeast extract agar medium are observed microscopically, hyphae are colorless and have septa. Conidiophores are directly grown from substrate mycelia and length is 175-730 μm with inverted T-form foot cells. A tip of the conidiophore becomes hypertrophied from globose to subglobose with forming vesicle with a diameter 15-60 μm. *Aspergilla* are biseriate and consisting of metulae (6-12×3-6 μm) and ampullar phialide (5-10×2-3 μm). Vesicle is covered almost all *Aspergilla*. Conidium is formed from a top of phialide, and grows to chain-like form depending upon culturing period. Conidium is globose to subglobose, pale orcher, sized 2-4 μm with rough surface.

2. Culturing Properties on Various Media

Results of macroscopic observation of the strain cultured on various agar media a 25° C. for 7 days are shown hereinbelow.

| Medium Growth condition on medium (diameter of colony) | Color of surface of colony | Color of reverse of colony | Soluble pigment |
|---|---|---|---|
| Czapeck yeast extract agar medium | | | |
| Good (60-65 mm) Flocky-velvety Wavy Smooth edge | white-cream | grayish-yellow | None |
| Malt extract agar medium | | | |
| Good (60-65 mm) Flocky-velvety Smooth edge | cream-pale ocher | gray | None |
| 20% sucrose Czapeck yeast extract agar medium | | | |
| Good (65-70 mm) Flocky-velvety Wavy Smooth edge | white-cream | cream-grayish yellow | None |

In addition, although the strain was cultured on Czapeck yeast extract agar medium at 5° C. and 37° C. for 14 days, no growth was observed.

3. Physiological Properties

1) Optimum Growth Condition

Optimum growth condition of the strain is pH 4-8 at 11.5-29° C.

2) Growth Range

Growth range of the strain is pH 3-10 at 10-30.5° C.

3) Nature for Growth Condition: Aerobic

4. International Deposition of Microorganism

Based on the morphological properties, culturing characteristics and physiological properties of the above FKI-2136 strain, as a result of comparison with known microbial species, the strain is identified as the strain belonging to genus *Aspergillus* and designated as *Aspergillus* sp. FKI-2136. The strain *Aspergillus* sp. FKI-2136 was deposited, according to the Budapest Treaty on the International Recognition of the Deposit of Microorganisms for the Purposes of Patent Procedure, in Incorporated Administrative Agency National Institute of Technology and Evaluation Patent Microorganisms Depositary (NPMD), 2-5-8 Kazusakamatari, Kisarazu-shi, Chiba-ken 292-0818 Japan. Date of deposit is Mar. 3, 2005 and accession number is NITE BP-83.

With regard to FKI-2136 substance producing microorganism strain used in the present invention, the strain *Aspergillus* sp. FKI-2136 hereinbefore can be mentioned as a preferable example. However, it is well known that the microorganism is very easily mutated in the general mycological properties and can not be maintained constant in the mycological properties, and is mutated by natural means or artificial means, for example commonly used ultraviolet irradiation or mutation inducer such as N-methyl-N'-nitro-N-nitrosoguanidine and 2-aminopurine. Consequently, the strains belonging to genus *Aspergillus* and having producing ability of stemphones represented by the chemical formula (I) and (II) hereinbefore, including artificial mutants and natural mutants, can be used all in the present invention.

The production of stemphones of the present invention can be performed at first by culturing FKI-2136 substance producing microorganism belonging to genus *Aspergillus*. As for nutrient sources preferable for production of the stemphones of the present invention, carbon sources which can be assimilable by microorganism, nitrogen sources which can be digestible, and if necessary nutrient medium containing inorganic salt, vitamin, etc. can be used. Examples of assimilable carbon sources are sugars such as glucose, fructose, maltose, lactose, galactose, dextrin and starch, and vegetable oil such as soybean oil. These are used alone or in combination.

Examples of digestible nitrogen sources are peptone, yeast extract, meat extract, soybean powder, cotton seed powder, corn steep liquor, malt extract, casein, amino acids, urea, ammonium salts and nitrate. These are used alone or in combination. If necessary, salts such as phosphate, magnesium salt, calcium salt, sodium salt and potassium salt, heavy metal salt such as iron salt, manganese salt, copper salt, cobalt salt and zinc salt, vitamins and substances preferable for stemphones production can be added.

In the culture, when forming occurs heavily, if necessary, antifoaming agent such as liquid paraffin, animal oil, vegetable oil, silicone oil and surface active agent can be added. The culture can be performed by liquid culture or solid culture, if above nutrient sources are contained. In general, the liquid medium may conveniently used for the culture. In case of small culture, the culture using flask is preferable. In case of industrial mass production of the objective substance, stirring aeration culture may be preferable as like in the other fermentation products.

In the large scale production using tank culture, in order to prevent growth delay of the microorganism in the production process, it is preferable that the production strain is at first inoculated and cultured in the relatively small amount of medium, and the cultured mass is transferred into the large tank and is continued to culture. In this case, composition of the medium used in the pre-cultivation and the medium used in the production culture can be same or if necessary it can be different.

When the culture is performed in aeration with stirring, known method such as stirring by propeller and other mechanical stirring, rotary or shaking the fermenter, pumping or bubbling aeration can be applied. Sterilized air is used for aeration.

Culturing temperature can be changed within ranges for production of the stemphones by the FKI-2136 substance producing strain, generally at 20-30° C., preferably around at 27° C. Culturing pH is generally 5-8, preferable around 7. Culturing time depends on the culturing condition and is generally 4-7 days. The stemphones accumulated in the thus obtained cultured mass is generally found in the cultured mycelia and cultured liquid. In order to collect the stemphones from the cultured mass, total cultured mass is subjected to extraction with water miscible organic solvent such as acetone, subsequently the organic solvent: is removed in vacuo from the extracted liquid, then the residue is extracted with water immiscible organic solvent such as ethyl acetate.

In addition to the above mentioned extraction methods, known methods used for collecting lipophilic substance, for example, adsorption chromatography, gel filtration chromatography, centrifugal countercurrent distribution chromatography, high performance liquid chromatography, etc. can be used alone or in combination, or repeatedly, thereby isolating and purifying the stemphones.

Physico-Chemical Properties

Physico-chemical properties of the stemphones of the present invention are explained as follows.

1. Stemphone B (1) Property: yellow needle (2) Molecular formula: $C_{30}H_{42}O_9$ HREI-MS (m/z) [M+] Calculated value: 546.2835, Measured value: 546.2829

(3) Molecular weight: 546

EI-MS (m/z) [M+] 546

(4) Ultraviolet absorption spectrum: UV spectrum measured in methanol solution is as shown in FIG. 1. λmax (MeOH, ε):Characteristic absorption maximum around at 206 nm (7748), 267 nm (5154), 383 nm (505)

(5) Infrared absorption spectrum: IR spectrum measured by KBr tablet is as shown in FIG. 2. νmax: Characteristic absorption maximum around at 3440, 2935, 1727, 1644, 1602 $cm^{-1}$ (6) Specific rotation: $[\alpha]_D^{26}$+144.0° (c=0.1, methanol)

(7) Solubility in solvent: Soluble in methanol and chloroform, and insoluble in water.

(8) Proton and carbon nuclear magnetic resonance spectra: Chemical shift of hydrogen (ppm) and that of carbon (ppm) measured in deuterated chloroform by using Varian 300 MHz NMR spectrometer are as shown hereinbelow.

$\delta_H$: 0.98 (3H), 1.04 (3H), 1.14 (3H), 1.20 (3H), 1.32 (3H), 1.58 (1H), 1.60 (1H), 1.61 (3H), 1.62 (3H), 1.86 (1H), 1.88 (1H), 1.94 (3H), 1.96 (1H), 2.08 (1H), 2.23 (1H), 3.30 (1H), 3.44 (1H), 3.57 (1H), 3.68 (1H), 4.10 (1H), 4.15 (1H), 4.90 (1H), 5.15 (1H), 5.56 (1H), 6.47 (1H) ppm, $\delta_c$: 11.6, 13.1, 13.2, 16.9, 21.2, 21.3, 23.8, 25.0, 26.4, 28.2, 34.2, 37.1, 40.8, 45.4, 62.3, 70.7, 71.7, 76.2, 79.6, 81.4, 83.8, 117.8, 125.3, 131.7, 132.6, 148.8, 151.5, 169.7, 181.0, 188.5 ppm As explained hereinabove, as a result of detailed examination on various physico-chemical properties and spectral data of stemphone B, stemphone B substance was determined to have chemical structure represented by the following formula (I)

2. Stemphone C (1) Property: yellow needle (2) Molecular formula: $C_{30}H_{42}O_7$ HREI-MS (m/z) [M+] Calculated value: 514.2926, Measured value: 514.2931

(3) Molecular weight: 514

EI-MS (m/z) [M+] 514

(4) Ultraviolet absorption spectrum: UV spectrum measured in methanol solution is as shown in FIG. 5. λmax (MeOH, ε): Characteristic absorption maximum around at 207 nm (7604), 265 nm (7239), 398 nm (616)

(5) Infrared absorption spectrum: IR spectrum measured by KBr tablet is as shown in FIG. 6. νmax: Characteristic absorption maximum around at 3444, 2944, 1739, 1643, 1604 $cm^{-1}$ (6) Specific rotation: $[\alpha]_D^{26}$+94.60 (c=0.1, methanol)

(7) Solubility in solvent: Soluble in methanol and chloroform, and insoluble in water.

(8) Proton and carbon nuclear magnetic resonance spectra: Chemical shift of hydrogen (ppm) and that of carbon (ppm) measured in deuterated chloroform by using Varian 300 MHz NMR spectrometer are as shown hereinbelow.

$\delta_H$: 0.88 (3H), 1.02 (3H), 1.16 (3H), 1.18 (3H), 1.21 (1H), 1.28 (3H), 1.43 (1H), 1.48 (1H), 1.59 (3H), 1.62 (3H), 1.63 (1H), 1.66 (1H), 1.79 (1H), 1.80 (1H), 1.86 (1H), 1.93 (3H), 2.11 (1H), 2.18 (1H), 2.52 (1H), 3.12 (1H), 3.21 (1H), 3.34 (1H), 5.14 (1H), 5.53 (1H), 6.48 (1H) ppm, $\delta_c$: 11.6, 12.2, 13.1, 16.4, 17.0, 20.8, 21.1, 21.3, 23.8, 25.2, 26.1, 33.5, 35.5, 36.8, 37.2, 46.6, 71.8, 80.5, 81.5, 84.0, 84.9, 117.8, 124.9, 132.1, 132.4, 148.0, 152.3, 169.8, 181.3, 187.1 ppm As explained hereinabove, as a result of detailed examination on various physico-chemical properties and spectral data of stemphone C, stemphone C substance was determined to have chemical structure represented by the following formula (II).

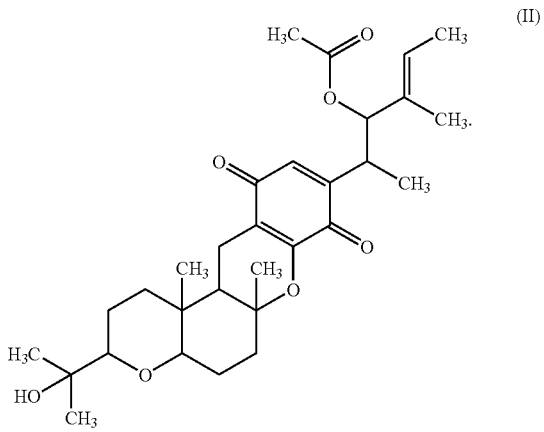

(II)

Biological data of stemphones are described in detail as follows.

1. Method for Evaluation of Enhancing Effect for Activity of Imipenem by Paper Disk Method Clinically isolated strain of methicillin resistant *Staphylococcus aureus* K24 was used as a test organism. *Staphylococcus aureus* was cultured in Mueller-Hinton broth (2.1% w/v) (DIFCO) at 37° C. for 20 hours, and was suspended corresponding to 0.5 Mc $F_{ARLAND}$ (about $10^8$ CFU/ml) in the same medium. The suspension was smeared on MHA medium (Mueller-Hinton broth 2.1% (w/v), agar 1.5%) and MHA medium added with imipenem (Banyu Seiyaku K. K., tienam for intramuscular injection, potency 0.5) to give a concentration for not to affect growth of the test organism, i.e. final concentration 10 μg/ml. Smearing was performed by using sterilized cotton swab (Kawamoto Sangyo K. K., Japan) according to a method of National Committee for Laboratory Standard, NCCLS, U.S.A. Antibacterial activities against test organism on various media were expressed with a unit in mm of a diameter of inhibition zone after incubation with the paper disc (thin disc, 6 mm, ADVANTEC Inc.) method at 37° C. for 20 hours. As a result, under the condition of 5 μg disc, the inhibitory zones were not observed by stemphone B and Stemphone C alone, whereas the inhibitory zones of 15 mm and 20 mm, respectively, were observed in the presence of imipenem. Consequently, enhancing activity for imipenem by stemphones was confirmed.

2. Method for Evaluation of Enhancing Activity Against Various Antimicrobial Agents by Broth Microdilution Method In addition to imipenem, enhancing activities of other antibacterial agents were evaluated on stemphone C, which shows strong enhancing activity for imipenem in the evaluation by the paper disk method. Other antibacterial agents used include cloxacillin (ICN Biomedicals Inc.), cefazolin (Wako Pure Chemical Industries, Ltd., Japan), vancomycin (Wako Pure Chemical Industries, Ltd., Japan), streptomycin (Meiji Seika Kaisha, Ltd., Japan), tetracycline (Wako Pure Chemical Industries, Ltd., Japan), erythromycin (Japan, stock of Kitasato University, Life Science Institute) and ciprofloxacin (Wako Pure Chemical Industries, Ltd., Japan). Evaluation was performed according to the modified standard method of Japan Society of Chemotherapy (CHEMOTHERAPY, 38:103-105, 1990).

Mueller-Hinton broth (2.1% w/v) 85 μl was added to each well of 96 well plate (Corning Corp., U.S.A.). 5 μl of imipenam, which was previously diluted with sterilized water by serial dilution method to give final concentration from $4.8 \times 10^{-4}$ to 256 μg/ml, were added to each well. Further, to each well was added 5 μl of methanol solution of stemphone C to give final concentration of 16 μg/ml, by which stemphone C itself did not affect growth of test organism. After mixing well, test organism MRSA was suspended corresponding to 0.5 Mc $F_{ARLAND}$ (about $10^8$ CFU/ml) in the same way as above. 5 μl of inoculum fluid prepared by diluting the suspension of test organism to tenfold with the same medium were inoculated into each well. After incubating at 37° C. for 20 hours, MIC was defined by minimum concentration of antibacterial agents in the well, which could not confirm the growth of test organism macroscopically. MIC of each antibacterial agent alone and MIC in combination with one of various antibacterial agents and stemphone C are shown in Table 1.

TABLE 1

| | MIC (μg/ml) | | Ratio |
|---|---|---|---|
| Antibacterial agent | − | +stemphone C | (−/+stemphone C) |
| imipenem | 16 | 0.03 | 512 |
| cloxacillin | 512 | 1 | 512 |
| cefazolin | 64 | 4 | 16 |
| vancomycin | 0.5 | 0.5 | 1 |
| streptomycin | 2 | 0.5 | 4 |
| tetracycline | 32 | 32 | 1 |
| erythromycin | >256 | >256 | 1 |
| ciprofloxacin | 64 | 32 | 2 |

As shown in the above, MIC of imipenem alone 16 μg/ml was reduced to MIC 0.03 μg/ml in the presence of stemphone C (16 μg/ml). Specifically, it was confirmed that the activity of imipenem was enhanced to 512-fold. Further, 512-fold and 16-fold enhanced activities were confirmed in cloxacillin and cefazolin, respectively. Consequently, stemphones had activity enhancing action for β-lactam antibiotics.

3. Antimicrobial Action Against Various Test Organisms

Paper disc method was used for measuring inhibitory zone (mm) in antimicrobial activity against 15 species of test organisms shown hereinbelow. Incubation temperature was set at 27° C. for *M. smegmatis, X. campestris* pv. *oryzae, P. oryzae, A. niger, M. racemosus, C. albicans* and *S. cerevisiae*, and at 37° C. for other test organisms. Incubation time was 48 hours for *M. smegmatis, P. oryzae* and *A. niger*, and 24 hours for other test organisms. Inhibitory zone (mm) of stemphones against each test organisms under the condition of drug concentration using 5 μg/disc with a diameter 6 mm was shown in Table 2.

TABLE 2

| | Inhibition zone (mm) | |
|---|---|---|
| Test strain | Stemphone B | Stemphone C |
| *Bacillus subtilis* KB211 (PCI 219) | 10 | 9 |
| *Stapylococcus aureus* KB210 (ATCC6538p) | 8 | 8 |
| *Micrococcus luteus* KB212 (ATCC9341) | 14 | 14 |
| *Mycobacterium smegmatis* KB42 (ATCC607) | — | — |
| *Escherichia coli* KB213 (NIHJ) | — | — |
| *Escherichia coli* KB176 (NIHJ $J_c$-2) | — | — |
| *Pseudomonas aeruginosa* KB105 (P-3) | — | — |
| *Xanthomonas campestris* pv. *oryzae* KB88 | — | — |

TABLE 2-continued

| Test strain | Inhibition zone (mm) | |
|---|---|---|
| | Stemphone B | Stemphone C |
| Bacteroides fragilis KB169 (ATCC23745) | — | — |
| Acholeplasma laidlawii KB174 | 10 | 9 |
| Pyricularia oryzae KB180 | — | — |
| Aspergillus niger KF103 (ATCC6275) | — | — |
| Mucor racemosus KF223 (IF04581) | — | — |
| Candida albicans KF1 | — | — |
| Saccharomyces cerevisiae KF237 (ATCC9763) | — | — |

BEST MODE FOR CARRYING OUT THE INVENTION

Figure 1:
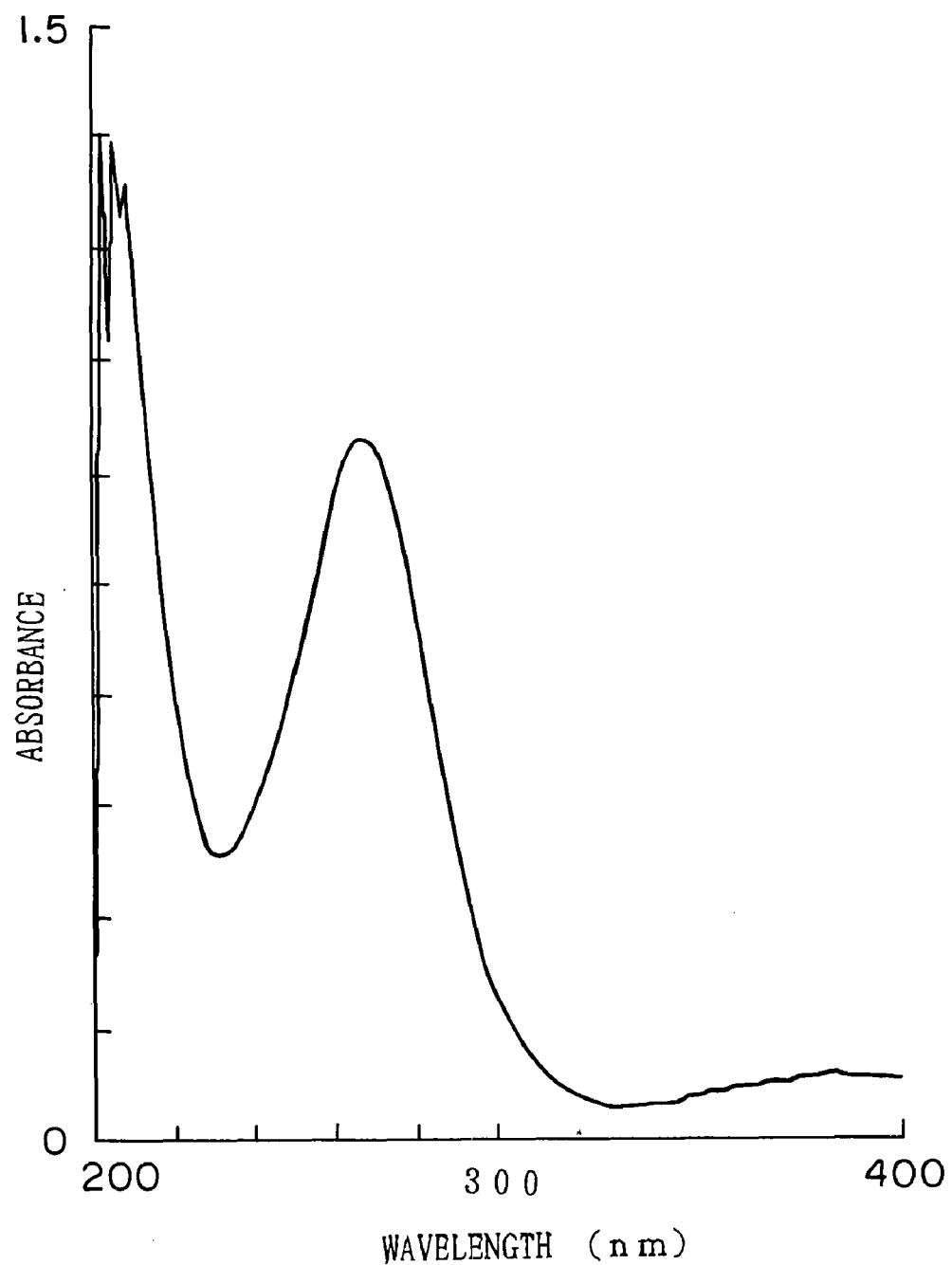
FIG. 1 shows ultraviolet spectrum of stemphone B (in methanol solution).
Figure 2:
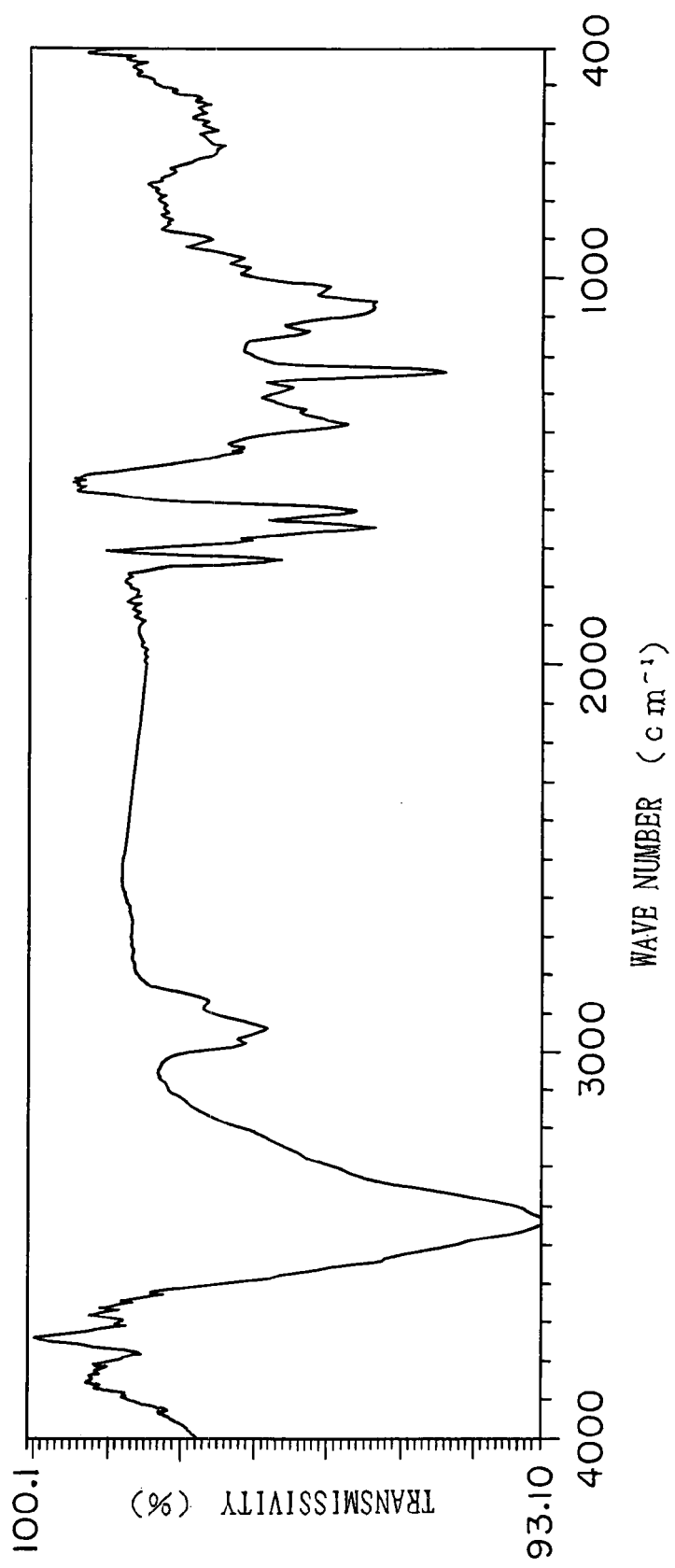
FIG. 2 shows infrared spectrum of stemphone B (KBr tablet).
Figure 3:
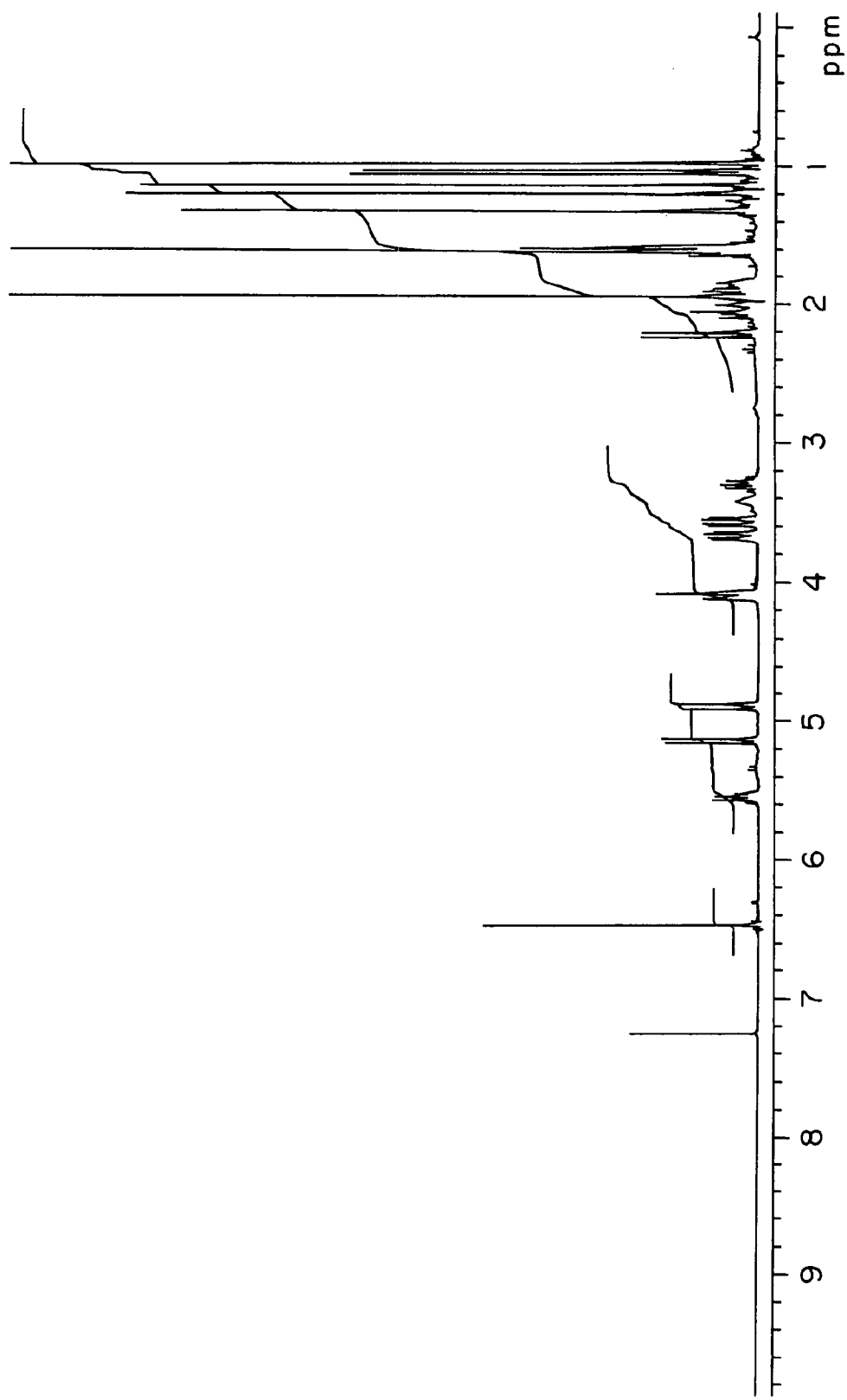
FIG. 3 shows proton nuclear magnetic resonance spectrum of stemphone B (in deuterated chloroform).
Figure 4:
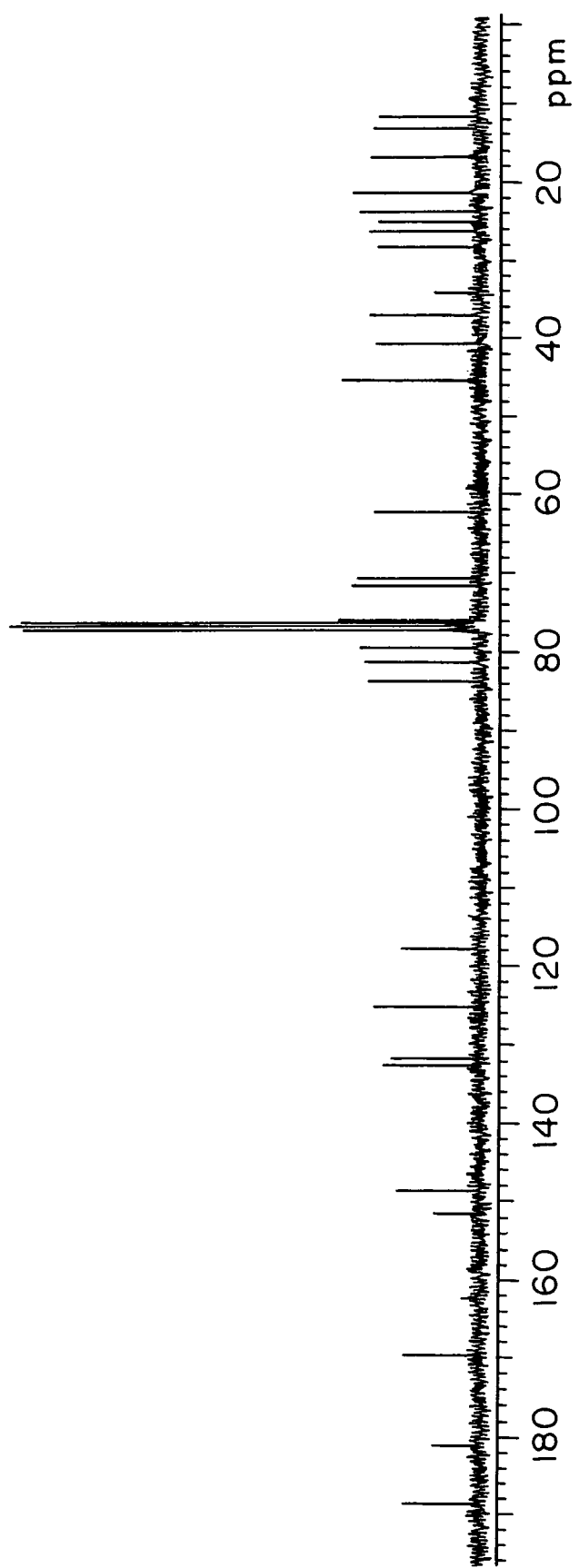
FIG. 4 shows carbon nuclear magnetic resonance spectrum of stemphone B (in deuterated chloroform).
Figure 5:
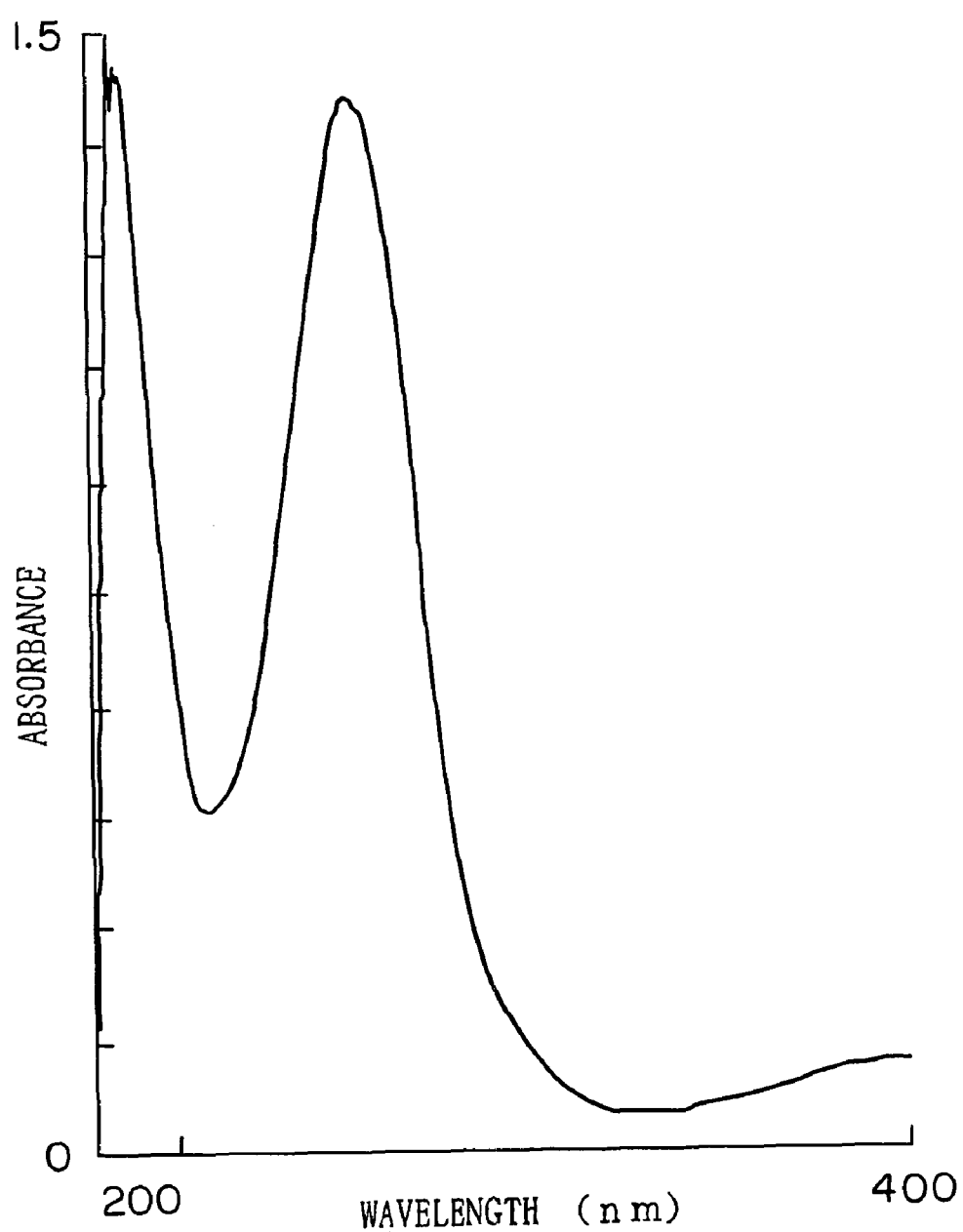
FIG. 5 shows ultraviolet spectrum of stemphone C (in methanol solution).
Figure 6:
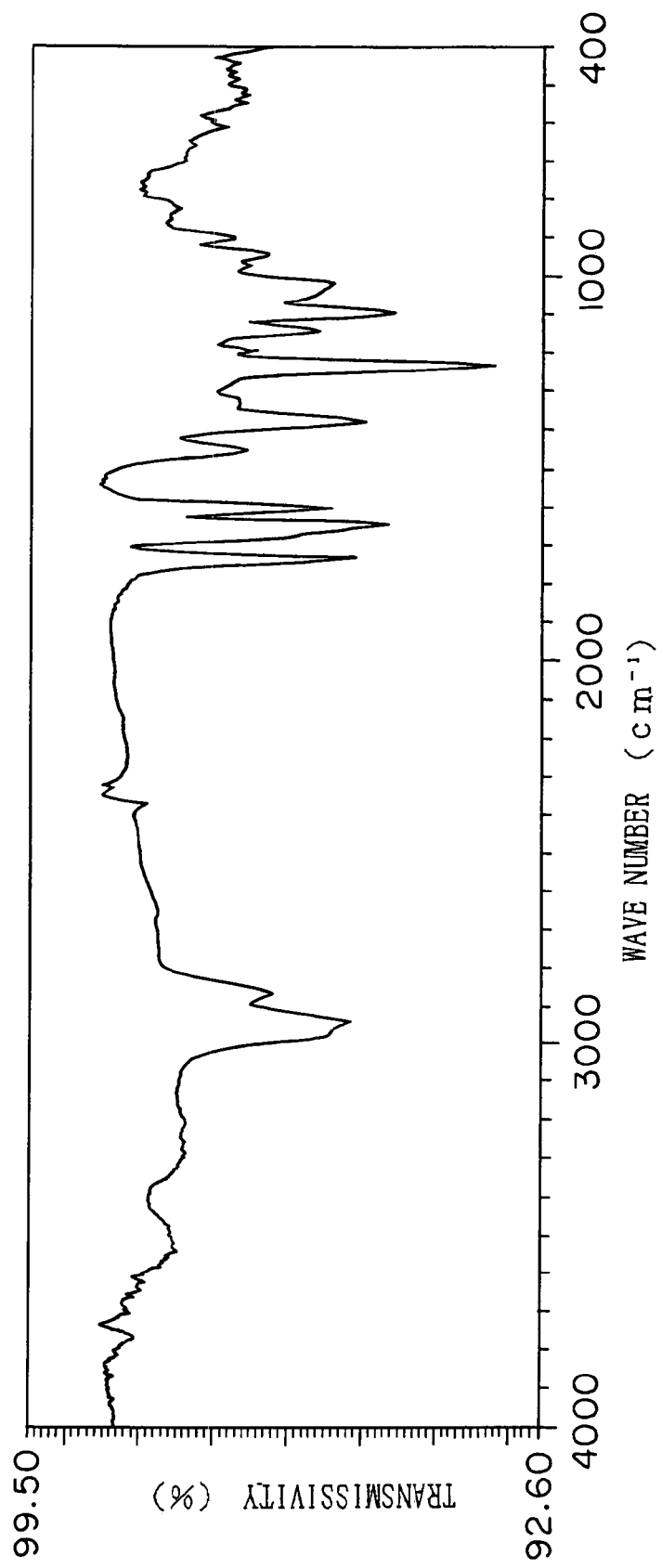
FIG. 6 shows infrared spectrum of stemphone C (KBr tablet).
Figure 7:
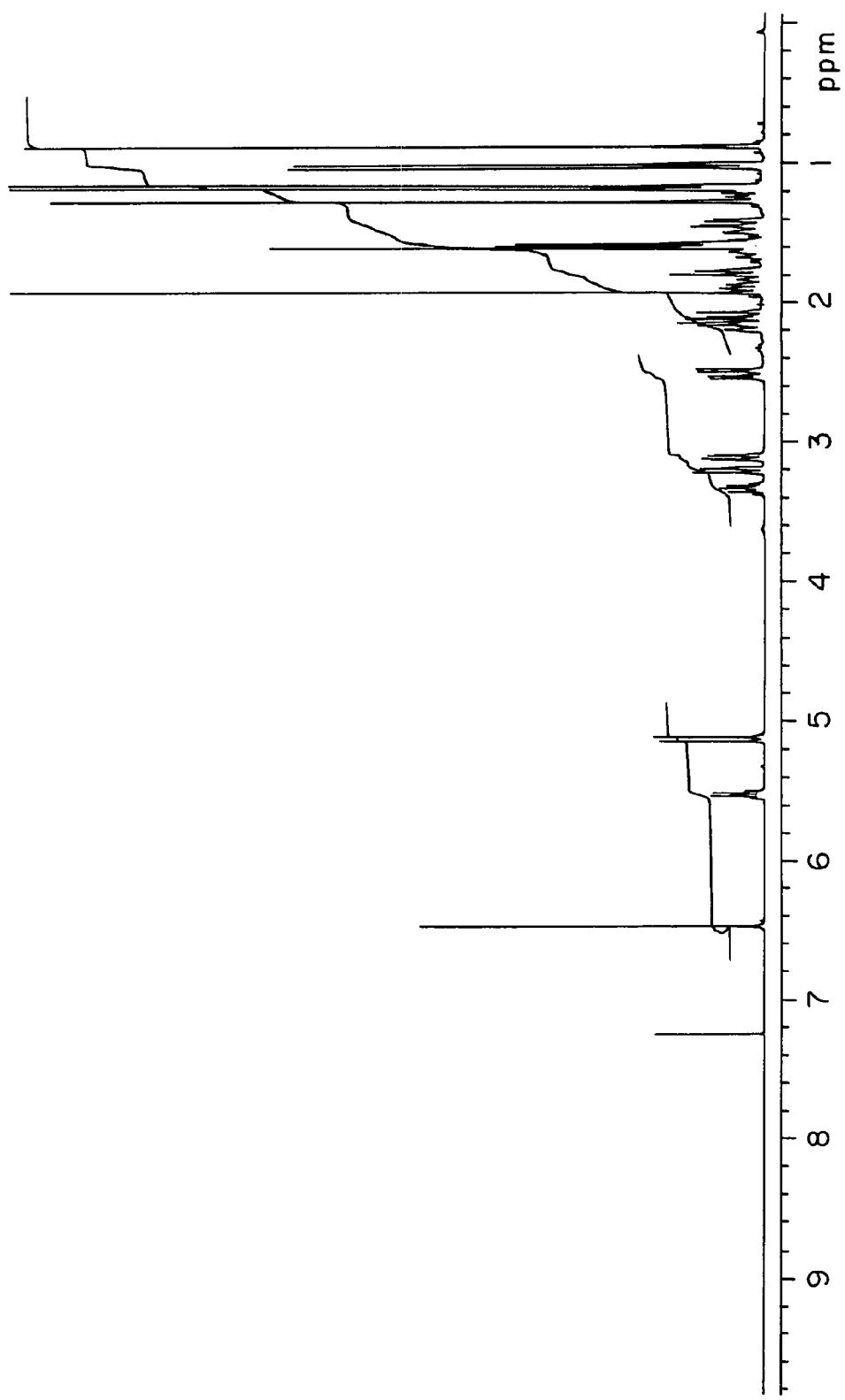
FIG. 7 shows proton nuclear magnetic resonance spectrum of stemphone C (in deuterated chloroform).
Figure 8:
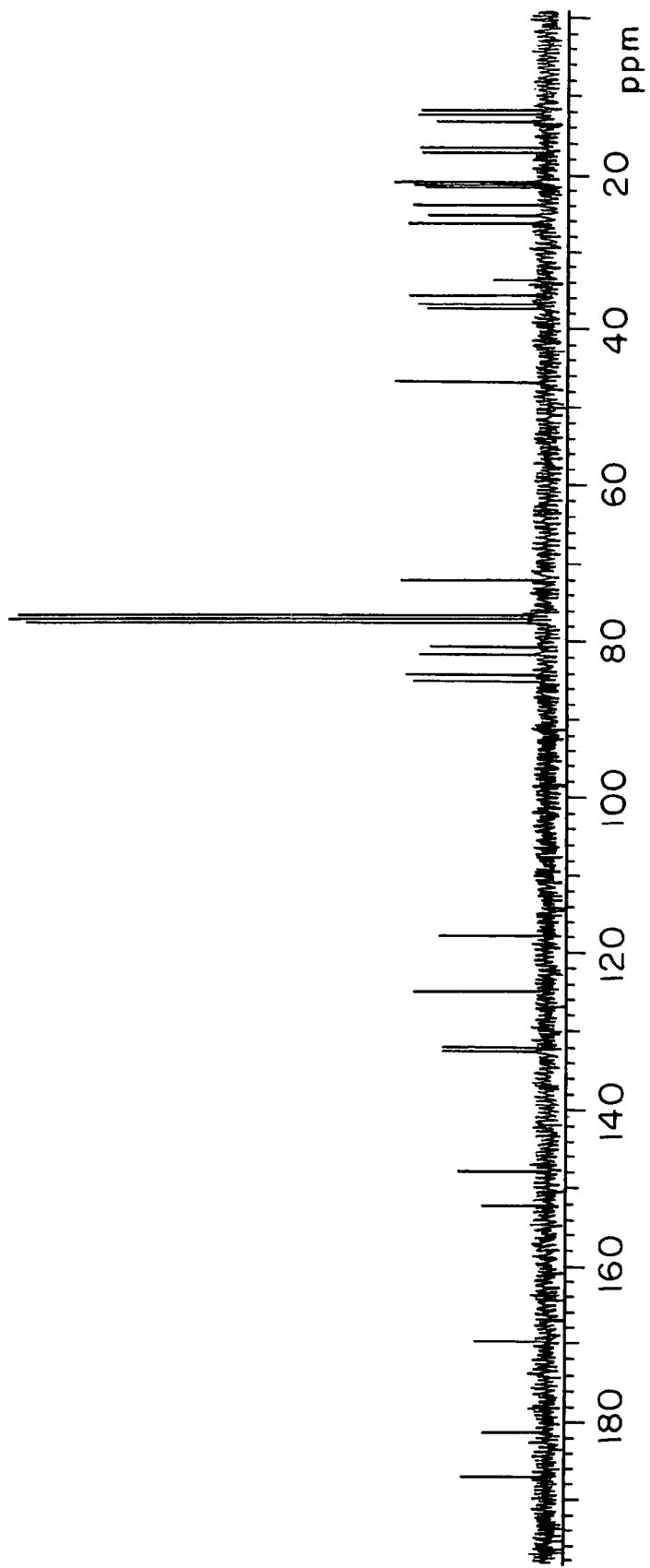
FIG. 8 shows carbon nuclear magnetic resonance spectrum of stemphone C (in deuterated chloroform).

The present invention is explained by mentioning example, but the present invention is not limited within the example.

Example

FKI-2136 strain (NITE BP-83) cultured on agar slant medium (glycerin 0.1% (Kanto Chemical Co., Inc., Japan), $KH_2PO_4$ 0.08% (Kanto Chemical Co., Inc., Japan), $K_2HPO_4$ 0.02% (Kanto Chemical Co., Inc., Japan), $MgSO_4.7H_2O$ 0.02% (Wako Pure Chemical Industries, Ltd., Japan), KCl 0.02% (Kanto Chemical Co., Inc., Japan), $NaNO_3$ 0.2% (Wako Pure Chemical Industries, Ltd., Japan), yeast extract 0.02% (Oriental Yeast Co., Ltd., Japan), and agar 1.5% (SHIMIZU SHOKUHIN KAISHA, LTD., Japan), adjusted to pH 6.0) was inoculated with each one loopful thereof in large test tube, to which 10 ml of seed culture medium (glucose 2% (Wako Pure Chemical Industries, Ltd., Japan), polypeptone 0.5% (Wako Pure Chemical Industries, Ltd., Japan), $MgSO_4.7H_2O$ 0.05% (Wako Pure Chemical Industries, Ltd., Japan), yeast extract 0.2% (Oriental Yeast Co., Ltd., Japan), $KH_2PO_4$ 0.1% (Kanto Chemical Co., Inc., Japan), and agar 0.1% (SHIMIZU SHOKUHIN KAISHA, LTD., Japan), adjusted to pH 6.0) was dispensed and cultured at 27° C. for 2 days on the rotary shaker (300 rpm). The seed cultured strain was inoculated into the 500 ml Erlenmeyer flask (30 flasks) dispensed with 100 ml of the production medium (glucose 1.0% (Wako Pure Chemical Industries, Ltd., Japan), soluble starch (Kanto Chemical Co., Inc., Japan), soybean oil 2.0% (Wako Pure Chemical Industries, Ltd., Japan), pharma media 1.0% (Iwaki & Co., Ltd., Japan) meat extract 0.5% (KYOKUTO PHARMACEUTICAL INDUSTRIAL CO., LTD., Japan), $MgSO_4.7H_2O$ 0.1% (Wako Pure Chemical Industries, Ltd., Japan), $CaCO_3$ 0.3% (Kanto Chemical Co., Inc., Japan), trace salt solution 1.0% ($FeSO_4.7H_2O$ 0.1% (Kanto Chemical Co., Inc., Japan), $MnCl_2.4H_2O$ 0.1% (Kanto Chemical Co., Inc., Japan), $ZnSO_4.7H_2O$ 0.1% (Kanto Chemical Co., Inc., Japan), $CuSo_4.5H_2O$ 0.1% (Kanto Chemical Co., Inc., Japan), $CoCl_2.6H_2O$ 0.1% (Wako Pure Chemical Industries, Ltd., Japan), and agar 0.1% (SHIMIZU SHOKUHIN KAISHA, LTD., Japan), adjusted to pH 6.0), and cultured at 27° C., 210 rpm, for 3 days. Thereafter, cultured medium was further transferred into 500 ml Roux flask (500 flasks), and standing cultured at 27° C. for 3 days.

After finishing the cultivation, the cultured fluid (3 lit.) was centrifuged to obtain supernatant and mycelia. Acetone (1.5 lit.) was added to the mycelia, stirred for 30 minutes and filtered the mycelia to obtain mycelial extract. Acetone was distilled off in vacuo from the mycelial extract to obtain aqueous residue. Active principle was extracted with ethyl acetate (9 lit.) from the aqueous residue, and the ethyl acetate layer was concentrated and dried in vacuo to obtain crude active substance (4.4 g). The crude substance was subjected to crude purification by silica gel column (silica gel, Merck, 40 g). After washing with mixed solvent of hexane—ethyl acetate (2:1), chromatography with developer solvent consisting of each mixed solvent of chloroform—methanol (100:0; 100:1; 50:1; 10:1; 5:1; and 1:1) was performed to fractionate into the eluate of 120 ml. Active fraction (10:1) was concentrated to dry to obtain brownish colored oily substance 786 mg. This crude substance was again purified by silica gel column (silica gel, Merck, 50 g). The chromatography with developer solvent consisting of each mixed solvent of chloroform-methanol (100:1; 50:1; 20:1; 10:1; and 5:1) was performed to fractionate into 10 tubes with each eluate of 12 ml. Active fractions (from 100:1 fraction No. 2 to 50:1 fraction No. 3) were concentrated to dry to obtain brownish colored oily substance 274 mg.

The substance was dissolved in small amount of methanol and was subjected to final purification by using preparative HPLC (column: PAGASIL ODS, 20 φ×250 mm, Senshu Scientific Co. Ltd., Japan). 70% aqueous acetonitrile solution was used as mobile phase, and UV absorption at 210 nm was monitored at the flow rate 6 ml/min. A peak at retention time 28 minutes showing activity was observed, and the peak was preparatively collected. The collected solution was concentrated in vacuo and residual aqueous solution was freeze dried to isolate stemphone C, yield 174 mg. Further, crude substance 262 mg obtained by concentrating and drying the active fraction (from fraction of 50:1 No. 4 to fraction of 20:1 No. 3) was dissolved in small amount of methanol and the solution was subjected to final purification by using preparative HPLC (column PEGASIL ODS, 20φ×250 mm). 55% aqueous acetonitrile solution was used as mobile phase, and UV absorption at 210 nm was monitored at the flow rate 9 ml/min. A peak at retention time 20 minutes was preparatively collected, and the collected solution was concentrated in vacuo and residual aqueous solution was freeze dried to isolate stemphone B, yield 58 mg.

INDUSTRIAL APPLICABILITY

As described hereinabove, since stemphones isolated from the culture fluid obtained by culturing microorganism represented by FKI-2136 strain belonging to genus *Aspergillus* having ability to produce novel stemphones in the medium have an action to enhance effect of β-lactam antibiotic utilized as antibacterial agent by combining with the β-lactam antibiotic, the stemphones are expected to be useful as the therapeutic agent for methicillin resistant *Staphylococcus aureus* (MRSA) infection and infectious diseases caused by multi-drug resistant microorganisms including β-lactam antibiotic resistance.

What is claimed is:

1. Stemphones selected from the group consisting of an isolated and purified stemphone B of formula (I):

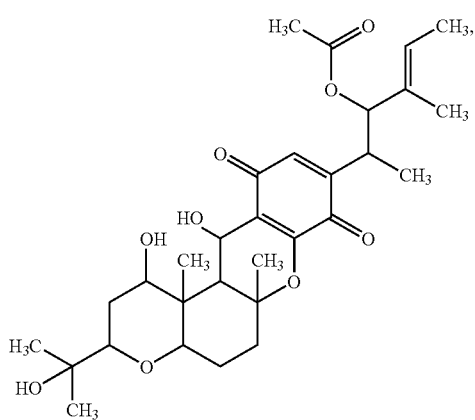

an isolated and purified stemphone C of formula (II):

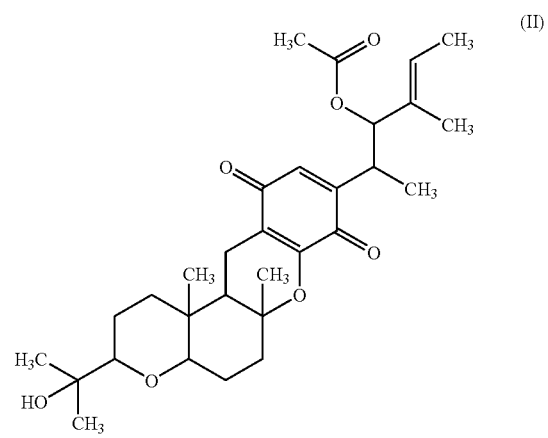

and a mixture thereof.

2. A process for production of stemphones I and/or II according to claim 1, comprising culturing *Aspergillus* sp. FKI-2136 NITE BP-83 or a mutant thereof having the ability to produce the stemphones of formula (I) and/or (II), accumulating the stemphone(s) in the cultured mass, and isolating the stemphone(s) from the cultured mass.

3. Stemphones according to claim 1, comprising an isolated and purified stemphone B.

4. Stemphones according to claim 1, comprising an isolated and purified stemphone C.

5. Stemphones according to claim 1, comprising an isolated and purified mixture of stemphones B and C.

* * * * *